(12) United States Patent
Lei et al.

(10) Patent No.: US 12,227,596 B2
(45) Date of Patent: Feb. 18, 2025

(54) ANTI-PHYSALIATOXIN SINGLE-DOMAIN ANTIBODY COZO32, PREPARATION METHOD, AND USE THEREOF

(71) Applicant: Naval Medical University, Shanghai (CN)

(72) Inventors: Changhai Lei, Shanghai (CN); Shi Hu, Shanghai (CN); Wenyan Fu, Shanghai (CN)

(73) Assignee: Naval Medical University, Shanghai (CN)

( * ) Notice: Subject to any disclaimer, the term of this patent is extended or adjusted under 35 U.S.C. 154(b) by 544 days.

(21) Appl. No.: 17/578,455

(22) Filed: Jan. 19, 2022

(65) Prior Publication Data

US 2022/0204648 A1 Jun. 30, 2022

(30) Foreign Application Priority Data

Dec. 30, 2020 (CN) .......................... 202011606833.4

(51) Int. Cl.
*C07K 16/40* (2006.01)
*A61K 39/00* (2006.01)
*A61P 39/02* (2006.01)

(52) U.S. Cl.
CPC .............. *C07K 16/40* (2013.01); *A61P 39/02* (2018.01); *A61K 39/00* (2013.01); *A61K 2039/505* (2013.01); *C07K 2317/569* (2013.01)

(58) Field of Classification Search
CPC .............. C07K 16/40; C07K 2317/569; C07K 2317/22; C07K 2317/92; C07K 2317/76; C07K 16/18; A61P 39/02; A61K 39/00; A61K 39/02; C12N 15/70
See application file for complete search history.

(56) References Cited

U.S. PATENT DOCUMENTS 9,128,089 B1 9/2015 Li et al.
9,631,010 B2 4/2017 Li et al.
9,771,423 B2 9/2017 Ghezzi et al.

OTHER PUBLICATIONS

De Genst et. al. (Molecular basis for the preferential cleft recognition by dromedary heavy-chain antibodies. Developmental and Comparative Immunology. vol. 30, pp. 187-198) (Year: 2006).*
Odom et. al. (Tissue-specific transcriptional regulation has diverged significantly between human and mouse. Nature Genetics. vol. 39(6), pp. 730-732) (Year: 2007).*
Vitetta et. al. (Considering therapeutic antibodies. Science. vol. 313, pp. 308-309) (Year: 2006).*

* cited by examiner

*Primary Examiner* — Chun W Dahle
*Assistant Examiner* — Albert A Serrano
(74) *Attorney, Agent, or Firm* — True Shepherd LLC; Andrew C. Cheng

(57) ABSTRACT

The present disclosure relates to the technical field of biomedicine, and provides an anti-physaliatoxin single-domain antibody, and a preparation method and use thereof. The single-domain antibody is a VHH antibody with an amino acid sequence shown in SEQ ID NO. 1. Affinity analysis shows that the single-domain antibody of the present disclosure has prominent affinity. It is proved by small animal experiments that, after mice in an antibody protection group pre-injected with the single-domain antibody of the present disclosure are injected with physaliatoxin, no mice shows toxic symptoms, and during continuous observation for one month, no toxic lethality occurs, indicating that the single-domain antibody of the present disclosure shows excellent anti-physaliatoxin effects, excellent preventive or therapeutic effects on jellyfish stings, and promising clinical application prospects.

6 Claims, No Drawings

Specification includes a Sequence Listing.

SEQUENCE LISTING

```
<160> NUMBER OF SEQ ID NOS: 2

<210> SEQ ID NO 1
<211> LENGTH: 127
<212> TYPE: PRT
<213> ORGANISM: Artificial Sequence
<220> FEATURE:
<223> OTHER INFORMATION: Designed amino acid sequence acting as an anti-
      physaliatoxin nanobody

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Ala Pro Trp Asp Ile Lys Val Ser Ser Tyr
            20                  25                  30

Ala Met Gly Trp Phe Arg Gln Ala Pro Gly Lys Arg Glu Gly Val Ala
        35                  40                  45
```

```
Ala His Arg Ala Lys Gly Gly Tyr Thr Tyr Thr Asp Ser Val Lys
    50                  55                  60

Gly Arg Phe Thr Ile Ser Arg Asp Asn Ala Lys Thr Val Tyr Leu
 65              70                  75                  80

Gln Met Asn Ser Leu Lys Pro Glu Asp Thr Ala Val Tyr Tyr Cys Ala
                85                  90                  95

Ala Ile Asp Met Lys His Thr Gly Ile Ala Ser Trp Gln Pro Val Phe
            100                 105                 110

Val Asn Met Tyr Trp Gly Gln Gly Thr Gln Val Thr Val Ser Ser
        115                 120                 125

<210> SEQ ID NO 2
<211> LENGTH: 381
<212> TYPE: DNA
<213> ORGANISM: Artificial Sequence
<220> FEATURE:
<223> OTHER INFORMATION: Designed nucleotide sequence acting as an anti-
      physaliatoxin nanobody

<400> SEQUENCE: 2
caggtgcagc tgcaggaaag cggcggcggc agcgtgcagg cgggcggcag cctgcgcctg      60
agctgcgcgc cgtgggatat taaagtgagc agctatgcga tgggctggtt tcgccaggcg     120
ccgggcaaac gcgaaggcgt ggcggcgcat cgcgcgaaag gcggctatac ctattatacc     180
gatagcgtga aaggccgctt taccattagc cgcgataacg cgaaaaccac cgtgtatctg     240
cagatgaaca gcctgaaacc ggaagatacc gcggtgtatt attgcgcggc gattgatatg     300
aaacataccg gcattgcgag ctggcagccg gtgtttgtga acatgtattg gggccagggc     360
acccaggtga ccgtgagcag c                                               381
```

ANTI-PHYSALIATOXIN SINGLE-DOMAIN ANTIBODY COZO32, PREPARATION METHOD, AND USE THEREOF

CROSS-REFERENCE TO RELATED APPLICATIONS

This application claims priority to Chinese Patent Application No. 202011606833.4 with a filing date of Dec. 30, 2020. The content of the aforementioned application, including any intervening amendments thereto, is incorporated herein by reference.

This application includes a Sequence Listing submitted electronically as a text file named US_SL_ST25.txt, created on Dec. 30, 2020, with a size of 2,162 bytes. The Sequence Listing is incorporated by reference herein.

TECHNICAL FIELD

The present disclosure belongs to the technical field of biomedicine, and specifically relates to an anti-jellyfish sting single-domain antibody COZO32, a preparation method thereof, and use thereof in the preparation of a physaliatoxin formulation.

BACKGROUND ART

Jellyfish is important plankton in the aquatic environment, and is one of the oldest and mysterious creatures worldwide. Jellyfish was present on the earth about 650 million years ago, which is distributed in almost all sea areas. In terms of classification, jellyfish includes Scyphozoa, Staurozoa, and Cubozoa of Cnidaria. The number of jellyfish has increased exponentially in recent decades, which leads to the destruction of marine ecosystems and causes catastrophic damage to marine fisheries. In addition, the number of jellyfish stings is increasing, and thousands of people are suffered every year, which has become a very troublesome issue.

Since the 1940s, related research on jellyfish stings of Portuguese man-of-war, Irukandji jellyfish, *Chironex fleckeri, Stomolophus meleagris, Cyanea capillata*, and other representative poisonous jellyfish, and treatment and poisoning mechanisms thereof have been concerned and gradually reported by Pubmed, and it is basically clear that systemic poisoning caused by jellyfish stings can be divided into two categories: local skin poisoning and systemic poisoning. Symptoms of the local skin poisoning include sharp pain, itching, skin rash, pigmentation, and the like; and symptoms of the systemic poisoning are caused by severe inflammatory responses after a jellyfish sting. If a person is soaked in physaliatoxin for a long time, the physaliatoxin is likely to penetrate through the skin and enter blood, which further causes extensive damage to multiple organs in the body such as heart, liver, and kidneys, thereby resulting in death.

At present, there are no therapeutic and preventive drugs for jellyfish stings. With the development of molecular biology, the technology of preparing physaliatoxin through genetic engineering has become matured, such that the biosynthesis of physaliatoxin can be realized, and research on the preparation of anti-physaliatoxin antibodies can be conducted on this basis.

Because antibodies can efficiently and specifically bind to various antigen proteins in vivo and in vitro, antibodies can not only be used to regulate the functions of immune systems, but also can be used for various detection methods with high sensitivity. At present, antibody drugs are the most important part of biotechnology drugs, and antibody reagents are also one of the most common reagents used in medical diagnosis and biological research. Therefore, antibody-related biological products have extremely-promising application prospects and extremely-high commercial values. Antibodies can be obtained from a variety of sources, such as animal or human blood, cell culture, and ascitic fluid of mice injected with hybridoma cells, but for all of these sources, an effective purification method is required to obtain antibody products with application values. At present, the most common method for antibody purification is affinity chromatography using the high affinity between a special protein and an Fc fragment of an antibody. Affinity chromatography is the most critical step in the industrial production of antibody products, and is also the most expensive part of the entire production.

In view of the above-mentioned problems, nanobodies have emerged, which are special antibodies derived from camelidae or cartilaginous fish. Studies have shown that there is an antibody that naturally lacks a light chain and only includes a heavy chain in camels, which is called a heavy-chain antibody (HCAb). A variable region of the HCAb can be cloned to obtain a single-domain antibody (sdAb) consisting only of one heavy-chain variable region, which is called a VHH antibody. A crystal of the VHH antibody is only 2.5 nm in diameter and 4 nm in length, and thus is also called a single-domain antibody. A size of the single-domain antibody is only one-tenth of a size of the traditional IgG antibody, and the single-domain antibody is the smallest natural fragment capable of binding to an antigen. The single-domain antibody can be encoded by a single gene, and can be easily produced by microorganisms, with a very high yield. However, there is no related report on anti-jellyfish sting nanobodies.

SUMMARY

The present disclosure is intended to study an anti-physaliatoxin single-domain antibody COZO32, and a preparation method and use thereof based on the above research background, that is, to provide a brand-new single-domain antibody, and a preparation method and use thereof.

In a first aspect of the present disclosure, a single-domain antibody COZO32 is provided, which is a VHH antibody and has an amino acid sequence shown in SEQ ID NO. 1; and a nucleotide sequence encoding the single-domain antibody is shown in SEQ ID NO. 2.

The amino acid sequence (SEQ ID NO. 1) of the single-domain antibody is as follows:

QVQLQESGGGSVQAGGSLRLSCAPWDIKVSSYAMGWFRQAPGKRE

GVAAHRAKGGYTYYTDSVKGRFTISRDNAKTTVYLQMNSLKPEDTAVYYC

AAIDMKHTGIASWQPVFVNMYWGQGTQVTVSS.

The nucleotide sequence (SEQ ID NO. 2) encoding the single-domain antibody is as follows:

CAGGTGCAGCTGCAGGAAAGCGGCGGCGGCAGCGTGCAGGCGGG

CGGCAGCCTGCGCCTGAGCTGCGCGCCGTGGGATATTAAAGTGAGCAGCT

ATGCGATGGGCTGGTTTCGCCAGGCGCCGGGCAAACGCGAAGGCGTGGC

GGCGCATCGCGCGAAAGGCGGCTATACCTATTATACCGATAGCGTGAAAG

-continued
GCCGCTTTACCATTAGCCGCGATAACGCGAAAACCACCGTGTATCTGCAGA

TGAACAGCCTGAAACCGGAAGATACCGCGGTGTATTATTGCGCGGCGATT

GATATGAAACATACCGGCATTGCGAGCTGGCAGCCGGTGTTTGTGAACAT

GTATTGGGGCCAGGGCACCCAGGTGACCGTGAGCAGC.

For the acquisition of the single-domain antibody, a single-domain antibody phage display library is first constructed, then the single-domain antibody is screened, specific positive clones are screened by phage enzyme-linked immunosorbent assay (ELISA), and after sequence analysis, the VHH single-domain antibody with the above amino acid sequence is obtained, which is composed of the FR1-CDR1-FR2-CDR2-FR3-CDR3-FR4 region. The single-domain antibody is expressed and purified in the host Escherichia coli (E. coli) to obtain a high-purity single-domain antibody.

In a second aspect of the present disclosure, a method for preparing the single-domain antibody is provided, including the following steps:
(A) synthesizing a VHH fragment of the single-domain antibody through gene synthesis;
(B) using polymerase chain reaction (PCR) to clone the VHH fragment of the single-domain antibody obtained in step (A), and purifying and recovering a PCR product by agarose gel electrophoresis; and cloning the PCR product into an expression vector, and conducting verification through sequencing to obtain a correct clone; and
(C) introducing the expression vector into a host cell for fusion protein expression.

In the present disclosure, any suitable vectors are applicable, which may preferably be pGEM-T, Pet32a, pcDNA3.1, pEE6.4, pEE12.4, pDHFR, or pDR1; and the expression vector may include a fusion DNA sequence ligated with appropriate transcription and translation regulatory sequences.

In the present disclosure, a mammalian or insect host cell or a prokaryotic cell culture system can be used for the expression of the fusion protein of the present disclosure. An available host cell may be a prokaryotic cell with the above-mentioned vector, which can be one from the group consisting of DH5a, Top10, BL21 (DE3), and TG1.

The fusion protein of the present disclosure can be easily produced in the following cells: mammalian cells, such as CHO, NSO, HEK293, BHK, or COS cells; bacterial cells, such as E. coli, Bacillus subtilis (B. subtilis), or Pseudomonas fluorescens (P. fluorescens); and insect cells, or fungal or yeast cells, which are cultivated using techniques known in the art.

The preparation method of the fusion protein disclosed in the present disclosure may include: cultivating the above-mentioned host cell under expression conditions to express, isolate, and purify the fusion protein. With the above method, the antibody can be purified into a substantially homogeneous substance, such as a single band of sodium dodecyl sulphate-polyacrylamide gel electrophoresis (SDS-PAGE).

The fusion protein disclosed in the present disclosure can be isolated and purified by affinity chromatography. According to characteristics of an affinity column used, a conventional method such as high-salt buffer and pH change can be used to elute the fusion protein peptide bound to the affinity column.

Various protein purification methods can be used, and such methods are known in the art and described in, for example, (Wilchek and Bayer, 1990, Methods in enzymology) (Scopes, 2013, Protein purification: principles and practice).

According to Biacore analysis, the single-domain antibody of the present disclosure has prominent affinity, and small animal experiments have shown that, after mice in a protection group pre-injected with the single-domain antibody of the present disclosure are injected with physaliatoxin, no mice shows neurotoxic symptoms, and during continuous observation for one month, no toxic lethality occurs. It indicates that the single-domain antibody of the present disclosure has an excellent anti-physaliatoxin effect.

Therefore, in a third aspect of the present disclosure, a pharmaceutical composition with the single-domain antibody is provided. In addition to the single-domain antibody, the pharmaceutical composition may include a pharmaceutically acceptable drug carrier.

The single-domain antibody of the present disclosure and a pharmaceutically acceptable adjuvant together constitute a pharmaceutical formulation composition, thereby exerting a more stable therapeutic effect. The formulation can ensure the conformational integrity of an amino acid core sequence of the single-domain antibody disclosed in the present disclosure, and can also protect multifunctional groups of the protein to prevent its degradation (including but not limited to aggregation, deamination, or oxidation).

Generally, a liquid formulation can remain stable at 2° C. to 8° C. for at least one year, and a lyophilized formulation can remain stable at 30° C. for at least six months. The formulation can be a suspension, an injection, a lyophilized formulation, or the like commonly used in the pharmaceutical field, and preferably an injection or a lyophilized formulation.

For the injection or lyophilized formulation of the single-domain antibody disclosed in the present disclosure, the pharmaceutically acceptable adjuvant may include one or a combination of two or more from the group consisting of a surfactant, a solution stabilizer, an isoosmotic adjusting agent, and a buffer. The surfactant may include a non-ionic surfactant, such as polyoxyethylene sorbitan fatty acid esters (Tween 20 or 80); poloxamer (such as poloxamer 188); Triton; sodium dodecyl sulfate (SDS), sodium lauryl sulfate (SLS); myristyl, linoleyl or stearyl sarcosine; Pluronics; and MONAQUAT™; and the surfactant may be added at an amount that minimizes the granulation tendency of the bifunctional bispecific antibody protein. The solution stabilizer can be sugar, including reducing sugar and non-reducing sugar; amino acid, including monosodium glutamate (MSG) or histidine; and alcohols, including one or a combination of two or more from the group consisting of triol, higher sugar alcohol, propylene glycol (PG), and polyethylene glycol (PEG); and the solution stabilizer may be added at an amount that enables a final formulation to remain stable within a period of time considered by those skilled in the art to reach a stable state. The isoosmotic adjusting agent can be one from the group consisting of sodium chloride and mannitol. The buffer can be one from the group consisting of tris(hydroxymethyl)aminomethane (TRIS), a histidine buffer, and a phosphate buffer.

The above-mentioned formulation is a composition including the single-domain antibody, and after being administered to animals including humans, the formulation shows a prominent anti-physaliatoxin effect. Specifically, the formulation is effective in preventing and/or treating jellyfish stings, and can be used as an anti-physaliatoxin drug.

In the present disclosure, when the single-domain antibody and the composition thereof are administered to animals including humans, a dosage varies with the age and body weight of the patient, the characteristics and severity of the disease, and the route of administration. The total dosage can be defined within a specified range with reference to results of animal experiments and various other conditions. Specifically, a dosage of intravenous injection may be 1 mg/d to 1,800 mg/d.

In a fourth aspect of the present disclosure, use of the single-domain antibody (specifically use in the preparation of an anti-physaliatoxin formulation drug) for preventing or treating jellyfish stings is provided.

The present disclosure has the following beneficial guarantees and effects:

The present disclosure provides an anti-physaliatoxin single-domain antibody, and a preparation method and use thereof. The single-domain antibody is a VHH antibody with an amino acid sequence shown in SEQ ID NO. 1, and has a size only one-tenth a size of the traditional IgG antibody. The single-domain antibody is the smallest natural fragment capable of binding to an antigen, which can be encoded by a single gene and can be easily produced by microorganisms. The construction and expression process is simple and has a high yield, which is conducive to industrial production.

In addition, affinity analysis shows that the single-domain antibody of the present disclosure has prominent affinity (with a KD value of 109.34 nM). It is proved by small animal experiments that, after mice in an antibody protection group pre-injected with the single-domain antibody of the present disclosure are injected with physaliatoxin, no mice shows toxic symptoms, and during continuous observation for one month, no toxic lethality occurs, indicating that the single-domain antibody of the present disclosure shows excellent anti-physaliatoxin effects, excellent preventive or therapeutic effects on jellyfish stings, and promising clinical application prospects.

DETAILED DESCRIPTION

The following examples and experimental examples are provided to further illustrate the present disclosure, and shall be construed as a limitation to the present disclosure. The examples do not include detailed descriptions of traditional methods, such as methods for constructing vectors and plasmids, methods for inserting genes encoding proteins into such vectors and plasmids, or methods for introducing plasmids into host cells. Such methods are well known to those of ordinary skill in the art, and are described in many publications, including Sambrook, J., Fritsch, E. F. and Maniais, T. (1989) Molecular Cloning: A Laboratory Manual, $2^{nd}$ edition, Cold spring Harbor Laboratory Press.

Example 1. Construction of a Single-Domain Antibody Library (1) 0.5 mg of physaliatoxin CfTX1 [Brinkman D, Burnell J. Partial purification of cytolytic venom proteins from the box jellyfish, *Chironex fleckeri* [J]. Toxicon, 2008, 51 (5): 853-863.] and a freund's adjuvant were mixed in equal volumes to immunize a Xinjiang Bactrian camel once a week, and a total of 6 consecutive immunizations were conducted. During the immunization process, B cells were stimulated to express a specific single-domain antibody.

(2) After the 6 immunizations were completed, 200 mL of peripheral blood lymphocyte (PBL) was collected from the camel to extract total RNA.

(3) cDNA was synthesized, and VHH was amplified by nested PCR.

(4) Restriction endonucleases Pstl and NotI were used to digest 20 μg of a pMECS phage display vector and 10 μg of VHH, and digestion products were ligated.

(5) A ligation product was electro-transformed into competent cells TG1, a phage display library was constructed, and a storage capacity thereof was determined, which was approximately $2.5\times10^{8}$. Moreover, an insertion rate of the library established was tested by colony PCR, which reached more than 95%.

Example 2. Single-Domain Antibody Screening Process (1) 200 μL of recombinant TG1 cell was inoculated and cultivated in a 2TY medium, and during the cultivation, 50 μL of helper phage VCSM13 was added to infect the TG1 cell and cultivated overnight to expand the phage; and the next day, the phage was precipitated with PEG/NaCl, and collected by centrifugation.

(2) 150 μg of physaliatoxin dissolved in 150 mmol/L pH 8.2 $NaHCO_3$ was coupled on an ELISA plate and incubated overnight at 4° C., and a negative control was set at the same time.

(3) The next day, 100 μL of 5% bovine serum albumin (BSA) was added to block at room temperature for 2 h.

(4) 2 h later, 100 μL of the phage ($1\times10^{11}$ tfu phage display gene library of the single-domain antibody of the immunized camel), and a resulting mixture was incubated at room temperature for 1 h.

(5) The plate was washed five times with phosphate buffered saline (PBS)+0.05% Tween 20 to remove unbound phage.

(6) Specifically-bound phages were dissociated with trypsin at a final concentration of 25 mg/mL, used to infect *E. coli* TG1 cells in logarithmic growth phase, and cultivated at 37° C. for 1 h; and resulting phages were collected for the next round of screening; and the same screening process was repeated 3 times to gradually achieve enrichment.

Example 3. Screening of Specific Positive Clones by Phage ELISA (1) 200 single colonies were picked from a cell culture plate obtained after the 3 rounds of screening and inoculated in a 96 deep-well plate with a 100 μg/mL ampicillinum-containing TB medium, and a blank control was set; and after the colonies were cultivated at 37° C. to a logarithmic phase, isopropyl-β-D-thiogalactoside (IPTG) at a final concentration of 1 mmol/L was added, and then the colonies were cultivated overnight at 28° C.

(2) A crude antibody was extracted by the osmotic burst method, transferred to an antigen-coated ELISA plate, and incubated at room temperature for 1 h.

(3) The unbound antibody was washed off with phosphate-buffered saline with Tween 20 (PBST), then 100 μL of Mouse anti-HA tag antibody (purchased from Covance) diluted at 1:2000 was added, and a resulting mixture was incubated at room temperature for 1 h.

(4) The unbound antibody was washed off with PBST, then 100 μL of Anti-mouse alkaline phosphatase conjugate (goat anti-mouse alkaline phosphatase-labeled antibody, purchased from Sigma) diluted at 1:2000 was added, and a resulting mixture was incubated at room temperature for 1 h.

(5) The unbound antibody was washed off with PBST, an alkaline phosphatase chromogenic solution was added to allow a reaction for 10 min, and an absorbance value was read at 405 nm on a microplate reader.

(6) When an OD value of a sample well was more than 6 times greater than that of a control well, the sample well was determined as a positive clone well. Results were shown in FIG. 1. An OD value of the SN160 well was significantly greater than that of the control well group.

(7) Bacteria in the positive clone well were transferred to a 100 μg/L ampicillinum-containing LB medium and cultivated under shaking, and then the plasmid was extracted and sequenced. Gene sequences of each cloned strain were analyzed according to the sequence alignment software Vector NTI. Strains with the same FR1, FR2, FR3, FR4, CDR1, CDR2, and CDR3 sequences were regarded as the same cloned strain, and strains with different sequences were regarded as different cloned strains. Finally, a specific single-domain antibody was obtained, with an amino acid sequence shown in SEQ ID NO. 1, and a nucleotide sequence encoding the antibody was shown in SEQ ID NO. 2.

Example 4. Expression and Purification of the Single-Domain Antibody in Host *E. coli*

(1) A clone obtained after the above sequencing analysis was transformed into *E. coli* WK6, and then the *E. coli* was coated on a culture plate with ampicillinum and glucose, and then cultivated overnight at 37° C.

(2) Single colonies were picked and inoculated into 5 mL of an ampicillinum-containing LB medium, and cultivated overnight at 37° C. on a shaker.

(3) 1 mL of a strain obtained after the overnight cultivation was inoculated into 330 mL of a TB medium and cultivated at 37° C. on a shaker until an $OD_{600\ nm}$ value reached 0.6 to 0.9, then 1 M IPTG was added, and then the strain was further cultivated overnight at 28° C. on a shaker.

(4) *E. coli* was collected by centrifugation, and the osmotic burst method was used to obtain a crude antibody extract.

(5) Purification was conducted by nickel column affinity chromatography to obtain a high-purity single-domain antibody, which was concentrated and enriched.

Example 5. Biacore Analysis

An anti-polyhistidine antibody (abcam) was coated on a CM5M5 chip (GE), and after the antibody to be tested was captured, the affinity of each fusion protein was detected by Biacore T100 (GE Healthcare). Specific detected affinity values were shown in Table 1.

TABLE 1

| Biacore analysis results | | |
|---|---|---|
| Parameter | Unit | Value |
| Binding affinity/kinetics | KD (nM) | 109.34 |

Example 6. Small Animal Experiment

32 C57 mice with a body weight of (20±2) g were selected and fasted for 12 h before the experiment (without water deprivation). The mice were randomly divided into three groups (half female and half male for each group): half-lethal dosage physaliatoxin group: 12 mice; drug protection group: 10 mice, which were pre-injected with the single-domain antibody at 10 mg/kg; and blank control group: 10 mice, which were administered with normal saline. The mice were administered intraperitoneally. Within 1 h after the administration, the mice in the blank control group all showed typical neurotoxic symptoms. None of the mice in the antibody protection group showed neurotoxic symptoms, and during continuous observation for one month, no toxic lethality occurred. Specific results were shown in Table 2.

TABLE 2

| Test results of the anti-physaliatoxin effect of the antibody | | | |
|---|---|---|---|
| | Total | Number of survivors on the day | Number of survivors after one month |
| Nanobody | 10 | 10 | 10 |
| Control group | 10 | 0 | 0 |

The preferred examples of the present disclosure have been described in detail above, but the present disclosure is not limited to these examples. Those skilled in the art can make various equivalent variations or substitutions without departing from the spirit of the present disclosure, and these equivalent variations or substitutions are all included in the scope defined by the claims of this application.

---

What is claimed is:

1. An anti-physaliatoxin single-domain antibody COZO32, wherein the single-domain antibody comprises the amino acid sequence shown in SEQ ID NO: 1.

2. A nucleotide sequence encoding the anti-physaliatoxin single-domain antibody COZO32 according to claim 1, wherein the nucleotide sequence comprises the sequence shown in SEQ ID NO: 2.

3. A pharmaceutical composition comprising the anti-physaliatoxin single-domain antibody COZO32 according to claim 1, wherein the pharmaceutical composition further comprises a pharmaceutically acceptable drug carrier.

4. A vector comprising the nucleotide sequence of claim 2.

5. A host cell comprising the vector of claim 4.

6. A method of producing an anti-physaliatoxin antibody by culturing the host cell of claim 5 and recovering the antibody from the culture.

* * * * *